(12) United States Patent
Tegeder et al.

(10) Patent No.: US 8,367,616 B2
(45) Date of Patent: Feb. 5, 2013

(54) USE OF A GRANULIN OR A GRANULIN-LIKE COMPOUND IN THE THERAPY OR PROPHYLAXIS OF CHRONIC PAINS

(75) Inventors: Irmgard Tegeder, Frankfurt (DE); Gerd Geisslinger, Bad Soden (DE)

(73) Assignee: Johann Wolfgang Goethe-Universitat Frankfurt am Main, Frankfurt am Main (DE)

( * ) Notice: Subject to any disclaimer, the term of this patent is extended or adjusted under 35 U.S.C. 154(b) by 122 days.

(21) Appl. No.: 12/668,147

(22) PCT Filed: Jul. 14, 2008

(86) PCT No.: PCT/DE2008/001138
§ 371 (c)(1),
(2), (4) Date: May 5, 2010

(87) PCT Pub. No.: WO2009/010045
PCT Pub. Date: Jan. 22, 2009

(65) Prior Publication Data
US 2010/0261657 A1    Oct. 14, 2010

(30) Foreign Application Priority Data
Jul. 16, 2007    (DE) .......................... 10 2007 033 359

(51) Int. Cl.
*A61K 38/16*    (2006.01)
*A61K 38/17*    (2006.01)

(52) U.S. Cl. ..................... 514/18.3; 514/21.2; 514/21.3; 530/300; 530/350

(58) Field of Classification Search ........................ None
See application file for complete search history.

(56) References Cited

FOREIGN PATENT DOCUMENTS

| EP | 1 164 144 A | 12/2001 |
|---|---|---|
| WO | WO 93/15195 A | 8/1993 |
| WO | WO 2004/078782 A | 9/2004 |
| WO | WO 2007/000924 A | 1/2007 |
| WO | WO 2008/019187 A | 2/2008 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Wang, W., et al., "PC cell-derived growth factor (Granulin precursor) expression and action in human multiple myeloma," *Clinical Cancer Research*, Jun. 1, 2003, pp. 2221-2228, vol. 9, No. 6.

* cited by examiner

*Primary Examiner* — Christine J Saoud
*Assistant Examiner* — Jon M Lockard
(74) *Attorney, Agent, or Firm* — Saliwanchik, Lloyd & Eisenschenk

(57) ABSTRACT

The invention relates to the use of a granulin or a granulin-like compound for producing a pharmaceutical composition for the therapy or prophylaxis of chronic pain, in particular for neuropathic pain.

6 Claims, 7 Drawing Sheets

Figure 1:
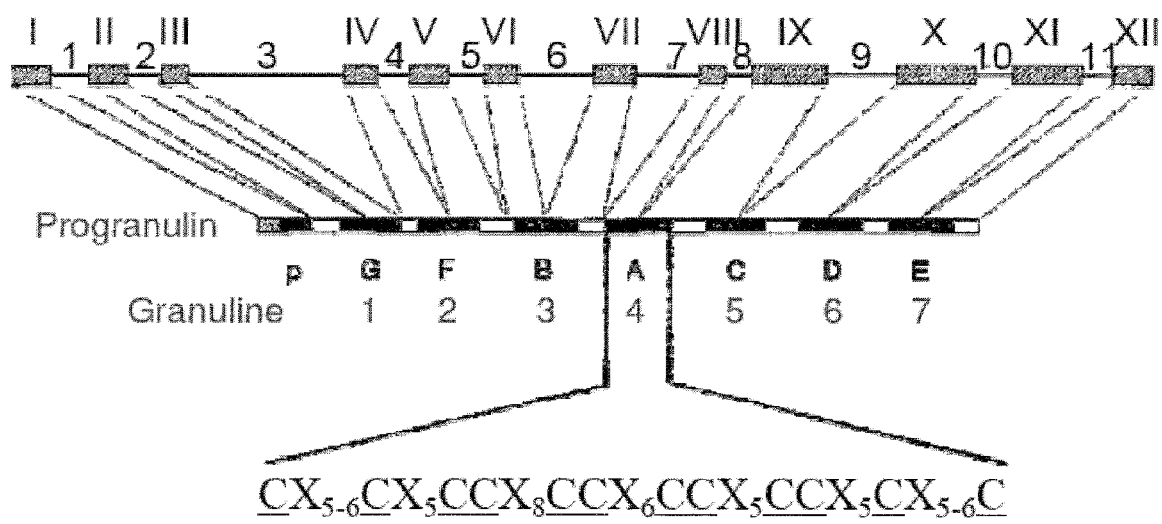

SEQUENCE LISTING

<160> NUMBER OF SEQ ID NOS: 20

<210> SEQ ID NO 1
<211> LENGTH: 2323
<212> TYPE: DNA
<213> ORGANISM: Homo sapiens

<400> SEQUENCE: 1

```
ggcgagagga agcagggagg agagtgattt gagtagaaaa gaaacacagc attccaggct      60
ggccccacct ctatattgat aagtagccaa tgggagcggg tagccctgat ccctggccaa     120
tggaaactga ggtaggcggg tcatcgcgct ggggtctgta gtctgagcgc tacccggttg     180
ctgctgccca aggaccgcgg agtcggacgc aggcagacca tgtggaccct ggtgagctgg     240
gtggccttaa cagcagggct ggtggctgga acgcggtgcc cagatggtca gttctgccct     300
gtggcctgct gcctggaccc cggaggagcc agctacagct gctgccgtcc ccttctggac     360
aaatggccca caacactgag caggcatctg ggtggcccct gccaggttga tgcccactgc     420
```

-continued

| | |
|---|---|
| tctgccggcc actcctgcat ctttaccgtc tcagggactt ccagttgctg cccttccca | 480 |
| gaggccgtgg catgcgggga tggccatcac tgctgcccac ggggcttcca ctgcagtgca | 540 |
| gacgggcgat cctgcttcca aagatcaggt aacaactccg tgggtgccat ccagtgccct | 600 |
| gatagtcagt tcgaatgccc ggacttctcc acgtgctgtg ttatggtcga tggctcctgg | 660 |
| gggtgctgcc ccatgcccca ggcttcctgc tgtgaagaca gggtgcactg ctgtccgcac | 720 |
| ggtgccttct gcgacctggt tcacacccgc tgcatcacac ccacgggcac ccacccctg | 780 |
| gcaaagaagc tccctgccca gaggactaac agggcagtgg ccttgtccag ctcggtcatg | 840 |
| tgtccggacg cacggtcccg gtgccctgat ggttctacct gctgtgagct gcccagtggg | 900 |
| aagtatggct gctgcccaat gcccaacgcc acctgctgct ccgatcacct gcactgctgc | 960 |
| ccccaagaca ctgtgtgtga cctgatccag agtaagtgcc tctccaagga aacgctacc | 1020 |
| acggacctcc tcactaagct gcctgcgcac acagtggggg atgtgaaatg tgacatggag | 1080 |
| gtgagctgcc cagatggcta tacctgctgc cgtctacagt cggggggcctg gggctgctgc | 1140 |
| ccttttaccc aggctgtgtg ctgtgaggac cacatacact gctgtcccgc ggggtttacg | 1200 |
| tgtgacacgc agaagggtac ctgtgaacag ggccccacc aggtgccctg gatggagaag | 1260 |
| gccccagctc acctcagcct gccagaccca caagccttga agagagatgt ccctgtgat | 1320 |
| aatgtcagca gctgtccctc ctccgatacc tgctgccaac tcacgtctgg ggagtggggc | 1380 |
| tgctgtccaa tcccagaggc tgtctgctgc tcggaccacc agcactgctg ccccagggc | 1440 |
| tacacgtgtg tagctgaggg gcagtgtcag cgaggaagcg agatcgtggc tggactggag | 1500 |
| aagatgcctg cccgccgggc ttccttatcc caccccagag acatcggctg tgaccagcac | 1560 |
| accagctgcc cggtggggca gacctgctgc ccgagcctgg gtgggagctg gcctgctgc | 1620 |
| cagttgcccc atgctgtgtg ctgcgaggat cgccagcact gctgcccggc tggctacacc | 1680 |
| tgcaacgtga aggctcgatc ctgcgagaag gaagtggtct ctgcccagcc tgccaccttc | 1740 |
| ctggcccgta gccctcacgt gggtgtgaag gacgtggagt gtggggaagg acacttctgc | 1800 |
| catgataacc agacctgctg ccgagacaac cgacagggc gggcctgctg tcctaccgc | 1860 |
| cagggcgtct gttgtgctga tcggcgccac tgctgtcctg ctggcttccg ctgcgcagcc | 1920 |
| aggggtacca agtgtttgcg cagggaggcc ccgcgctggg acgccccttt gagggaccca | 1980 |
| gccttgagac agctgctgtg agggacagta ctgaagactc tgcagccctc gggacccac | 2040 |
| tcggagggtg ccctctgctc aggcctccct agcacctccc cctaaccaaa ttctccctgg | 2100 |
| accccattct gagctcccca tcaccatggg aggtggggcc tcaatctaag gccttccctg | 2160 |
| tcagaagggg gttgtggcaa aagccacatt acaagctgcc atcccctccc cgtttcagtg | 2220 |
| gaccctgtgg ccaggtgctt ttccctatcc acagggtgt ttgtgtgtgt gcgcgtgtgc | 2280 |
| gtttcaataa agtttgtaca ctttcaaaaa aaaaaaaaa aaa | 2323 |

<210> SEQ ID NO 2
<211> LENGTH: 165
<212> TYPE: DNA
<213> ORGANISM: Homo sapiens

<400> SEQUENCE: 2

| | |
|---|---|
| ggcccctgcc aggttgatgc ccactgctct gccggccact cctgcatctt taccgtctca | 60 |
| gggacttcca gttgctgccc cttcccagag gccgtggcat gcgggatgg ccatcactgc | 120 |
| tgcccacggg gcttccactg cagtgcagac gggcgatcct gcttc | 165 |

```
<210> SEQ ID NO 3
<211> LENGTH: 171
<212> TYPE: DNA
<213> ORGANISM: Homo sapiens

<400> SEQUENCE: 3
gccatccagt gccctgatag tcagttcgaa tgcccggact tctccacgtg ctgtgttatg      60
gtcgatggct cctggggggtg ctgccccatg ccccaggctt cctgctgtga agacagggtg    120
cactgctgtc cgcacggtgc cttctgcgac ctggttcaca cccgctgcat c              171

<210> SEQ ID NO 4
<211> LENGTH: 168
<212> TYPE: DNA
<213> ORGANISM: Homo sapiens

<400> SEQUENCE: 4
gtcatgtgtc cggacgcacg gtcccggtgc cctgatggtt ctacctgctg tgagctgccc      60
agtgggaagt atggctgctg cccaatgccc aacgccacct gctgctccga tcacctgcac    120
tgctgccccc aagacactgt gtgtgacctg atccagagta agtgcctc                  168

<210> SEQ ID NO 5
<211> LENGTH: 168
<212> TYPE: DNA
<213> ORGANISM: Homo sapiens

<400> SEQUENCE: 5
gatgtgaaat gtgacatgga ggtgagctgc ccagatggct atacctgctg ccgtctacag      60
tcgggggcct ggggctgctg ccctttttacc caggctgtgt gctgtgagga ccacatacac   120
tgctgtcccg cggggtttac gtgtgacacg cagaagggta cctgtgaa                  168

<210> SEQ ID NO 6
<211> LENGTH: 162
<212> TYPE: DNA
<213> ORGANISM: Homo sapiens

<400> SEQUENCE: 6
gtcccctgtg ataatgtcag cagctgtccc tcctccgata cctgctgcca actcacgtct      60
ggggagtggg gctgctgtcc aatcccagag gctgtctgct gctcggacca ccagcactgc    120
tgcccccagg gctacacgtg tgtagctgag gggcagtgtc ag                        162

<210> SEQ ID NO 7
<211> LENGTH: 165
<212> TYPE: DNA
<213> ORGANISM: Homo sapiens

<400> SEQUENCE: 7
atcggctgtg accagcacac cagctgcccg gtggggcaga cctgctgccc gagcctgggt      60
gggagctggg cctgctgcca gttgcccat gctgtgtgct gcgaggatcg ccagcactgc    120
tgcccggctg gctacacctg caacgtgaag gctcgatcct gcgag                     165

<210> SEQ ID NO 8
<211> LENGTH: 168
<212> TYPE: DNA
<213> ORGANISM: Homo sapiens

<400> SEQUENCE: 8
gacgtggagt gtggggaagg acacttctgc catgataacc agacctgctg ccagacaac       60 cgacagggct gggcctgctg tcctaccgc cagggcgtct gttgtgctga tcggcgccac    120
```

```
tgctgtcctg ctggcttccg ctgcgcagcc aggggtacca agtgtttg          168
```

<210> SEQ ID NO 9
<211> LENGTH: 90
<212> TYPE: DNA
<213> ORGANISM: Homo sapiens

<400> SEQUENCE: 9

```
acgcggtgcc cagatggtca gttctgccct gtggcctgct gcctggaccc cggaggagcc    60
agctacagct gctgccgtcc ccttctggac                                     90
```

<210> SEQ ID NO 10
<211> LENGTH: 51
<212> TYPE: DNA
<213> ORGANISM: Homo sapiens

<400> SEQUENCE: 10

```
atgtggaccc tggtgagctg ggtggcctta acagcagggc tggtggctgg a            51
```

<210> SEQ ID NO 11
<211> LENGTH: 593
<212> TYPE: PRT
<213> ORGANISM: Homo sapiens

<400> SEQUENCE: 11

```
Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255
```

```
Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
            290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
                340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
            370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
            450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
            530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 12
<211> LENGTH: 56
<212> TYPE: PRT
<213> ORGANISM: Homo sapiens

<400> SEQUENCE: 12

Gly Gly Pro Cys Gln Val Asp Ala His Cys Ser Ala Gly His Ser Cys
1               5                   10                  15

Ile Phe Thr Val Ser Gly Thr Ser Cys Cys Pro Phe Pro Glu Ala
                20                  25                  30
```

```
Val Ala Cys Gly Asp Gly His His Cys Cys Pro Arg Gly Phe His Cys
        35                  40                  45

Ser Ala Asp Gly Arg Ser Cys Phe
    50                  55
```

<210> SEQ ID NO 13
<211> LENGTH: 57
<212> TYPE: PRT
<213> ORGANISM: Homo sapiens

<400> SEQUENCE: 13

```
Ala Ile Gln Cys Pro Asp Ser Gln Phe Glu Cys Pro Asp Phe Ser Thr
1               5                   10                  15

Cys Cys Val Met Val Asp Gly Ser Trp Gly Cys Cys Pro Met Pro Gln
            20                  25                  30

Ala Ser Cys Cys Glu Asp Arg Val His Cys Cys Pro His Gly Ala Phe
        35                  40                  45

Cys Asp Leu Val His Thr Arg Cys Ile
    50                  55
```

<210> SEQ ID NO 14
<211> LENGTH: 56
<212> TYPE: PRT
<213> ORGANISM: Homo sapiens

<400> SEQUENCE: 14

```
Val Met Cys Pro Asp Ala Arg Ser Arg Cys Pro Asp Gly Ser Thr Cys
1               5                   10                  15

Cys Glu Leu Pro Ser Gly Lys Tyr Gly Cys Cys Pro Met Pro Asn Ala
            20                  25                  30

Thr Cys Cys Ser Asp His Leu His Cys Cys Pro Gln Asp Thr Val Cys
        35                  40                  45

Asp Leu Ile Gln Ser Lys Cys Leu
    50                  55
```

<210> SEQ ID NO 15
<211> LENGTH: 56
<212> TYPE: PRT
<213> ORGANISM: Homo sapiens

<400> SEQUENCE: 15

```
Asp Val Lys Cys Asp Met Glu Val Ser Cys Pro Asp Gly Tyr Thr Cys
1               5                   10                  15

Cys Arg Leu Gln Ser Gly Ala Trp Gly Cys Cys Pro Phe Thr Gln Ala
            20                  25                  30

Val Cys Cys Glu Asp His Ile His Cys Cys Pro Ala Gly Phe Thr Cys
        35                  40                  45

Asp Thr Gln Lys Gly Thr Cys Glu
    50                  55
```

<210> SEQ ID NO 16
<211> LENGTH: 54
<212> TYPE: PRT
<213> ORGANISM: Homo sapiens

<400> SEQUENCE: 16

```
Val Pro Cys Asp Asn Val Ser Ser Cys Pro Ser Ser Asp Thr Cys Cys
1               5                   10                  15

Gln Leu Thr Ser Gly Glu Trp Gly Cys Cys Pro Ile Pro Glu Ala Val
            20                  25                  30
```

-continued

```
Cys Cys Ser Asp His Gln His Cys Cys Pro Gln Gly Tyr Thr Cys Val
            35                  40                  45
Ala Glu Gly Gln Cys Gln
        50

<210> SEQ ID NO 17
<211> LENGTH: 55
<212> TYPE: PRT
<213> ORGANISM: Homo sapiens

<400> SEQUENCE: 17

Ile Gly Cys Asp Gln His Thr Ser Cys Pro Val Gly Gln Thr Cys Cys
1               5                   10                  15
Pro Ser Leu Gly Gly Ser Trp Ala Cys Cys Gln Leu Pro His Ala Val
            20                  25                  30
Cys Cys Glu Asp Arg Gln His Cys Cys Pro Ala Gly Tyr Thr Cys Asn
            35                  40                  45
Val Lys Ala Arg Ser Cys Glu
        50                  55

<210> SEQ ID NO 18
<211> LENGTH: 56
<212> TYPE: PRT
<213> ORGANISM: Homo sapiens

<400> SEQUENCE: 18

Asp Val Glu Cys Gly Glu Gly His Phe Cys His Asp Asn Gln Thr Cys
1               5                   10                  15
Cys Arg Asp Asn Arg Gln Gly Trp Ala Cys Cys Pro Tyr Arg Gln Gly
            20                  25                  30
Val Cys Cys Ala Asp Arg Arg His Cys Cys Pro Ala Gly Phe Arg Cys
            35                  40                  45
Ala Ala Arg Gly Thr Lys Cys Leu
        50                  55

<210> SEQ ID NO 19
<211> LENGTH: 30
<212> TYPE: PRT
<213> ORGANISM: Homo sapiens

<400> SEQUENCE: 19

Thr Arg Cys Pro Asp Gly Gln Phe Cys Pro Val Ala Cys Cys Leu Asp
1               5                   10                  15
Pro Gly Gly Ala Ser Tyr Ser Cys Cys Arg Pro Leu Leu Asp
            20                  25                  30

<210> SEQ ID NO 20
<211> LENGTH: 17
<212> TYPE: PRT
<213> ORGANISM: Homo sapiens

<400> SEQUENCE: 20

Met Trp Thr Leu Val Ser Trp Val Ala Leu Thr Ala Gly Leu Val Ala
1               5                   10                  15
Gly
```

USE OF A GRANULIN OR A GRANULIN-LIKE COMPOUND IN THE THERAPY OR PROPHYLAXIS OF CHRONIC PAINS

CROSS-REFERENCE TO A RELATED APPLICATION

This application is a National Stage Application of International Application Number PCT/DE2008/001138, filed Jul. 14, 2008; which claims priority to German Application No. 10 2007 033 359.7, filed Jul. 16, 2007, which are incorporated herein by reference in their entirety, including sequences, tables and figures.

The invention relates to the use of a granulin or a granulin-like compound for the production of a pharmaceutical composition for the therapy or prophylaxis of chronic pain, in particular for the production of pharmaceutical compositions for the therapy or prophylaxis of chronic pain. Furthermore, the invention relates to a respective pharmaceutical composition.

In patients that suffered from neuronal damages, whether traumatic, inflammatory, infectious, tumor-related, ischemic, degenerative, metabolic or toxic, often secondary neuronal damages, such as cellular death and chronic pain, in particular neuropathic pain, take place as a cause of these neuronal damages.

Neuropathic pain can emerge from manifold damages of peripheral and central neuronal cells Pain is common in, amongst others, diabetic or toxic (such as, for example, due to a chemo-therapeutical therapy) polyneuropathy, phantom pains following amputation, postzosteric neuralgia, trigeminus neuralgia, compression syndrome, such as the carpal tunnel syndrome, and ischialgia in spinal prolaps, pain in multiple sclerosis and post-ischemic neuralgia. The non-invasive medicamentous possibilities that are known from the state of the art are limited to the use of different antiepileptics (e.g. gabapentin, pregabalin), anti-depressives (e.g. amitrytilin) and opioids, which, nevertheless, can only achieve a sufficient analgetic effect with simultaneously tolerable side effects in only about 30% of the patients, and do not influence the neuronal damage.

The mechanisms that contribute to the generation of chronic, in particular neuropathic, pain are diverse. Experimental studies in recent years show that the transsynaptic destruction of inhibitory neurons and the activation of glial cells essentially add to this.

Accordingly, it is an object of the present invention to provide a method or a means, respectively, which can be used for the therapy or prophylaxis of a neuronal damage, in order to particularly favour the regeneration in partially peripheral neuronal lesions, and to prevent the secondary cellular death.

The quintessence of the present invention consists in the reduction of the loss of inhibitory neurons and the block of the glial-mediated inflammatory reaction through the therapeutic use of a neuroprotective compound, and thus to avoid a progressing damage through continuous overexcitement. This reduces chronic, in particular neuropathic, pain, and supports regenerative processes.

The object underlying the invention is solved by the use of a granulin or a granulin-like compound for producing a pharmaceutical composition for the therapy and/or prophylaxis of chronic pain. Therein, the term "chronic pain", amongst others, comprises neuropathic pain, and inflammatory and tumor-related pain.

The use of a granulin or a granulin-like compound for the therapy or prevention of chronic, in particular neuropathic, pain in an acute or chronic neuronal damage represents a new therapeutic principle that, in contrast to the available medicamentous possibilities (antiepileptics, antidepressives, opioids, and cannabioids), positively influences the pathophysiologically underlying mechanisms.

According to the invention, it is possible to avoid the destruction of inhibitory interneurons. In doing so, the insufficient blocking of excitatory impulses, and thus the overactivity of pain-transmitting tracts, is avoided. The chronification of neuropathic pain is therefore reduced through the resulting limitation of the remodelling processes and misconnections that occur due to the apoptosis of inhibitory neurons. In contrast to this, the medicaments that are available until now lead to a general damping of the neuronal activity and do not influence the pathophysiological mechanisms in neuropathic pain resulting from peripheral or central neuronal damage.

In a preferred embodiment of the invention, the granulin or a granulin-like compound is at least one molecule selected from the group containing progranulin, granulin 1, granulin 2, granulin 3, granulin 4, granulin 5, granulin 6, granulin 7, paragranulin, progranulin signaling molecule, and fragments of these molecules that are functionally equivalent to these molecules, and an agonist that is functionally equivalent to these molecules. As will be further discussed below, the agonist particularly can be a peptidomimetic.

In addition, the use of combinations of different molecules from the above-mentioned group is included in the present invention.

Basically, the invention relates to both proteins or peptides, respectively, and nucleic acids, such as DNA, cDNA or RNA, as well as their derivatives.

Accordingly, in one embodiment of the invention the granulin or the granulin-like compound can be a nucleic acid encoding for one of said molecules. In particular, the nucleic acid can be a nucleic acid according to one of SEQ. ID. NOs. 1 to 10 or a nucleic acid that is identical to at least 50%, preferably to 60%, 70% or 80%, in particular preferably to 85% or 90%, most preferred to 95% or 98% to one of these sequences. Thereby, the peptide or protein that is encoded by the nucleic acid is advantageously functionally equivalent to a granulin or a granulin-like compound according to SEQ. ID. NO. 11 to 20.

A fragment of a nucleic acid shall mean an arbitrary sequence of at least 50, preferably of at least 150, particularly preferred of at least 180 continuous nucleotides from the sequence of granulin or a granulin-like compound found in a nucleic acid encoding granulin or a granulin-like compound.

The nucleic acid encoding for a functionally equivalent fragment is identical to at least 50%, preferably to 60%, 70% or 80%, in particular to 85% or 90%, most preferably to 95% or 98% with respect to the nucleic acid encoding for said fragment from SEQ. ID. NO. 11 to 20.

"Functionally equivalent" shall mean a fragment that has the same qualitative effect on neurons and glial cells as a granulin or a granulin-like compound according to SEQ. ID. NOs. 11 to 20, wherein the quantitative effect can be different.

Alternatively to this, in another embodiment of the invention the granulin or the granulin-like compound can be a protein or a peptide. In particular, the peptidomimetic as already mentioned above has to be mentioned here.

In a particularly preferred embodiment the granulin or the granulin-like compound is a protein or a peptide according to one SEQ. ID. NOs. 11 to 20 or a peptide or protein that is identical to at least 50%, preferably to 60%, 70% or 80%, in particularly preferred to 85% or 90%, most preferably to 95% or 98% to one of these sequences.

A fragment of proteins or peptides shall mean an arbitrary sequence present in a granulin or a granulin-like compound of at least 5, preferably of at least 10 or at least 20, particularly preferably of at least 30, 40, most preferably of at least 50 continuous amino acids from the sequence of granulin or a granulin-like compound.

The above described compound is suitable for producing pharmaceutical compositions for the therapy or prophylaxis of chronic, in particular neuropathic pain, in mammals, in particular in a human, but also in pets and livestock. The present invention is described with respect to human nucleic acid and protein/peptide sequences. Nevertheless, the person of skill, based on the human sequences and using known methods, can also detect the sequences of other species, as long as they are not contained in the publicly available databases.

The use as described above is also suitable for the production of pharmaceutical compositions for the reduction of neuropathic pain, the avoidance of cellular death of damaged neurons, and/or for the promotion of the neuronal regeneration.

The underlying problem of the invention is also solved by a pharmaceutical composition comprising and/or containing a granulin or a granulin fragment functioning equivalently, or a granulin-agonist.

Thereby, the granulin or the granulin-like compound is preferably at least one molecule selected from a group containing progranulin, granulin 1, granulin 2, granulin 3, granulin 4, granulin 5, granulin 6, granulin 7, paragranulin, progranulin signaling molecule, fragments of the aforementioned molecules that are functioning equivalently, and agonists (e.g. a peptidomimetic that is not one of the aforementioned fragments) of these molecules that are functioning equivalently.

In analogy to the above description, the granulin or the granulin-like compound of the pharmaceutical composition can be a nucleic acid encoding for one of said molecules, in particular a nucleic acid according to one of the SEQ. ID. NOs. 1 to 10 or a nucleic acid that is at least 50%, preferably to 60%, 70% or 80%, in particular preferably to 85% or 90%, most preferably to 95% or 98% identical to one of these sequences. Thereby, the encoded peptide or protein is equivalently effective in the sense of the above definition.

The said nucleic acids can be administered to a patient through transfer of a construct comprising said sequences, such as, for example, viruses or plasmids, into at least one cell. The transfection of the constructs can take place by means of known methods, such as lipofection, ballistic transfer ("gene gun"), etc.

In an alternative embodiment, the granulin or the granulin-like compound of the pharmaceutical composition is a protein or a peptide. Thereby, it is advantageous if the granulin or the granulin-like compound is a protein or a peptide according to one of the SEQ. ID. NOs. 11 to 20 or a protein or peptide that is identical to one of the sequences to at least 50%, preferably to 60%, 70% or 80%, in particular preferably to 85% or 90%, most preferably to 95% or 98%.

The pharmaceutical composition as described can preferably be used for producing pharmaceutical compositions for the therapy or prophylaxis of chronic, in particular neuropathic, pain in mammals, in particular in pets and livestock, and in the human. Although the sequences as given here are all derived from the human, based on the sequences as given here the skilled person can identify and isolate the corresponding molecules in other organisms.

According to the invention, the pharmaceutical composition can also serve for producing pharmaceutical compositions for the reduction of chronic, in particular neuropathic pain, avoidance of the cellular death of damaged neurons, and/or the promotion of the neuronal regeneration.

The pharmaceutical composition according to the invention can be present in the form of tablets, dragees, pills, granulates, aerosols, infusion solutions, emulsions, suspensions or solutions.

The use of the agents or the pharmaceutical composition according to the invention, respectively, can take place using suitable known formulations.

The use of the agents according to the invention can be converted in a known manner into the common formulations, such as tablets, dragees, pills, granulates, aerosols, emulsions, suspensions and solutions, using inert, non toxic, pharmaceutically acceptable carriers or solvents. Hereby, the therapeutically effective concentration of agent in relation to the granulin or the granulin-like compounds shall be present in the overall mixture in a concentration of about 0.1 wt.-% to 95 wt.-%, preferably of about 0.5 wt.-% to 90 wt.-%, respectively, i.e. in amounts that are sufficient in order to achieve the concentration of agent as required in the tissue as targeted.

The formulations are, for example, produced by stretching of the agents with solvents and/or carriers, optionally using emulsifiers and/or dispersants, wherein, for example in case of using water as a diluent, optionally organic solvents can be used as auxiliary agents.

Mentioned as auxiliary agents shall be, for example, water, non-toxic solvents, such as paraffin (e.g. crude oil fractions), plant oils (e.g. peanut, sesame oil), alcohols (e.g. ethyl alcohol, glycerol), carriers, such as natural stone dusts (e.g. kaolins, alumina, talcum, chalk), synthetic stone dusts (e.g. highly disperse silica, silicates), sugars (e.g. cane, milk and grape sugar), emulgators (e.g. polyoxyethylene fatty acid esters, polyoxyethylene fatty acid ethers), dispersants (e.g. lignin, spent sulfite liquors, methyl cellulose, starch and polyvinyl pyrrolidone) and lubricants (e.g. magnesium stearate, talcum, stearic acid and sodium sulfate).

The application takes place in a common way, preferably orally or parenterally, in particular perlingually or intravenously. In case of the oral use of the medicaments according to the invention, tablets can naturally also contain additives, such as sodium citrate, calcium carbonate and dicalcium phosphate, together with several additives, such as starch, preferably potato starch, gelatine, and the like, in addition to the carriers as mentioned. Furthermore, lubricants, such as magnesium stearate, sodium lauryl sulphate and talcum can be included for tabletting. In case of aqueous suspensions, several taste improving agents or colouring agents can be added to the active agents in addition to the above mentioned auxiliary agents. In case of a parenteral administration, solutions of the active agents using suitable liquid carrier materials can be employed.

The invention also relates to the use of a granulin or a granulin-like compound as described here for the therapy or prophylaxis of neuropathic pain, or a granulin or a granulin-like compound as described here and its use for the therapy or prophylaxis of neuropathic pain.

The invention also relates to a method for the therapy or prophylaxis of an individual, in particular of a patient, using a granulin or a granulin-like compound or a pharmaceutical composition according to the description as above.

The invention is further explained based on examples, without being limited to these examples. The results of the experiments as described in the examples are shown in the Figures.

FIGURES

FIG. 1: Progranulin is a cysteine-rich protein, which is cleaved by yet unknown proteases into seven different granulins (FIG. 1) that are secreted, and like the starting product exhibit growth factor and cytokine-like effects, promote wound healing, regulate tumour growth, and neuronal development. Until now, extra- and intracellular "receptors" are unknown. In the human, a "loss-of-function" mutation of the progranulin-gene causes a fronto-temporal dementia. Intron-exon-structure of the human gene for progranulin Grn, exons are depicted as boxes. The progranulin-protein is cleaved by proteases into 7 different granulins (black boxes) and an N-terminal "signalling peptide". All granulins have a structure similar to granulin A (Cx-Cx-CCx-CCx-CCx-CCx-Cx-C). C=cysteine, X=variable number of other amino acids.

Figure 2:
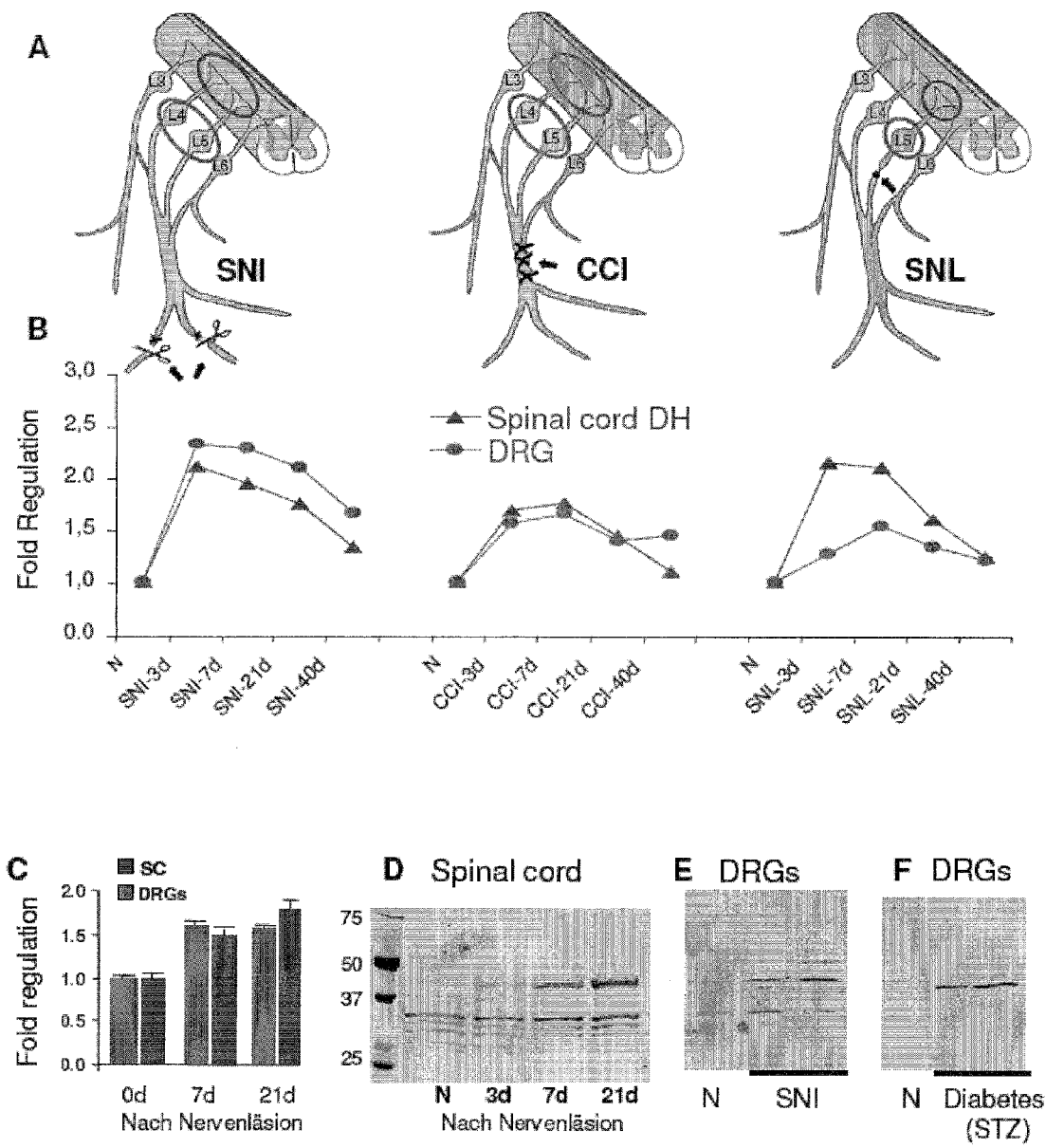

FIG. 2: Regulation of the progranulin-expression in the spinal cord and DRGs after peripheral lesion of the *N. ischiadicus*.
A Neuropathic models, Spared Nerve Injury (SNI, Decosterd & Woolf), Chronic Constriction Injury (CCI, Bennett), Spinal Nerve Ligation (SNL, Chung).
B Microarray analysis of the progranulin mRNA in the dorsal horn and DRGs in the models shown above.
C Quantitative RT-PCR of the progranulin mRNA in the SNI model.
D Western Blot analysis of the progranulin protein expression in the spinal cord in the SNI model.
E Progranulin-protein in DRGs after SNI.
F Progranulin-protein expression in DRGs in STZ induced diabetes polyneuropathy-model, 3 months after diabetes induction.

Figure 3:
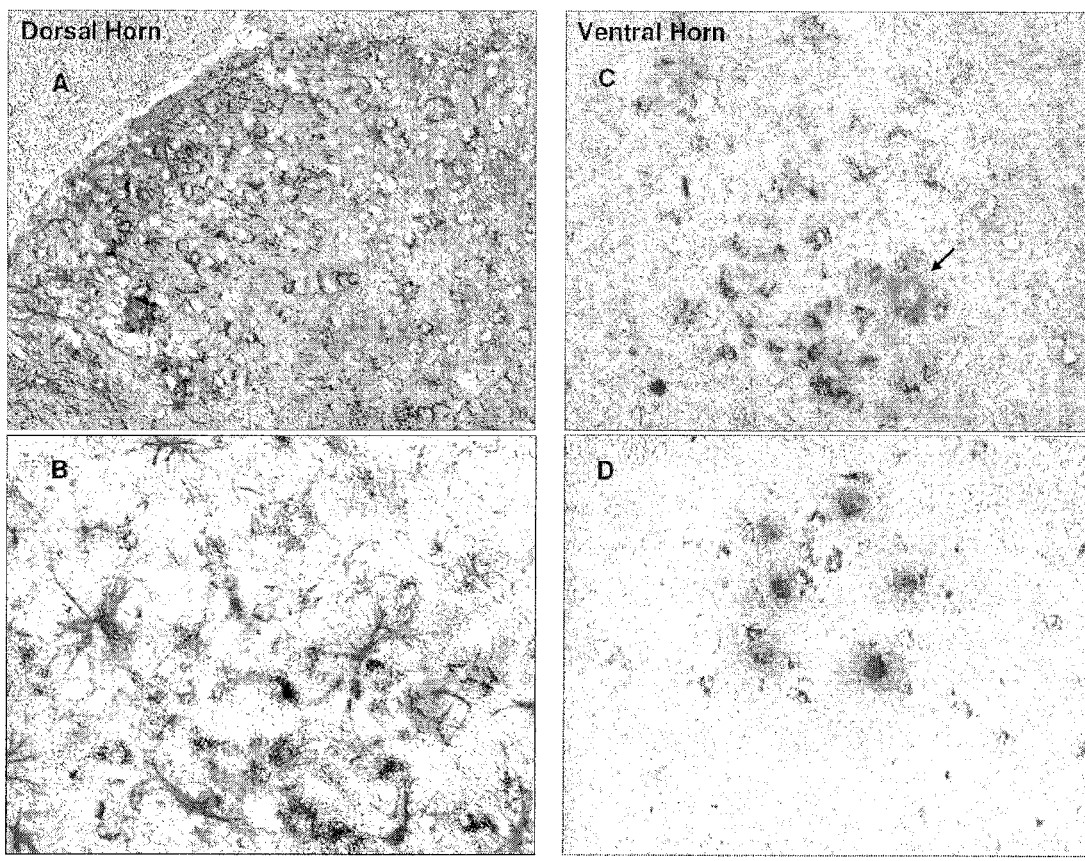

FIG. 3: Progranulin in situ hybridisation and post-in situ immunofluorescence for glial fibrillary acid protein, GFAP and the transcription factor ATF-3.
A Grn in situ (black) and GFAP immunofluorescence (red) for demonstrating the astrocytes after SNI in the dorsal horn of the spinal cord.
B Higher magnification of A. Progranulin is not expressed in astrocytes.
C Grn in situ (black) in microglial (small cells) and motor neurons (arrow) in the anterior horn of the spinal cord after SNI.
D Anterior horn as in C with demonstration of damaged motor neurons by ATF-3 immunofluorescence (red). ATF-3 is a marker for neurons with damaged axon.

Figure 4:
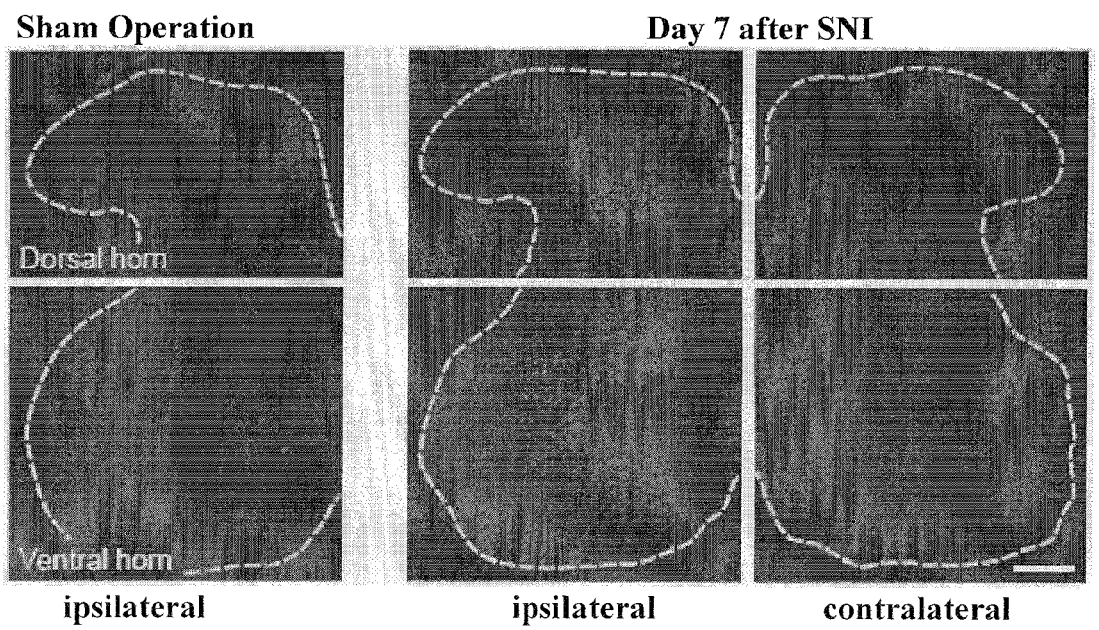

FIG. 4: Overview of the microglial reaction in the spinal cord after SNI. Demonstration of the microglia by immunofluorescence for the receptor of the complement factor 3 (CD11b).

Figure 5:
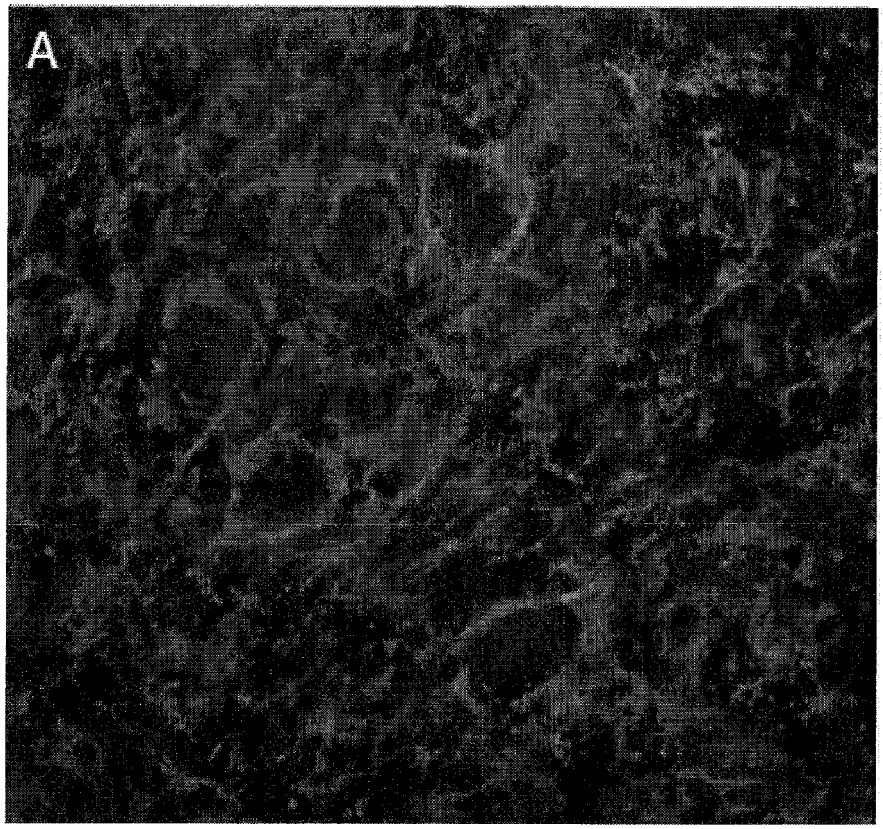
Figure 5:
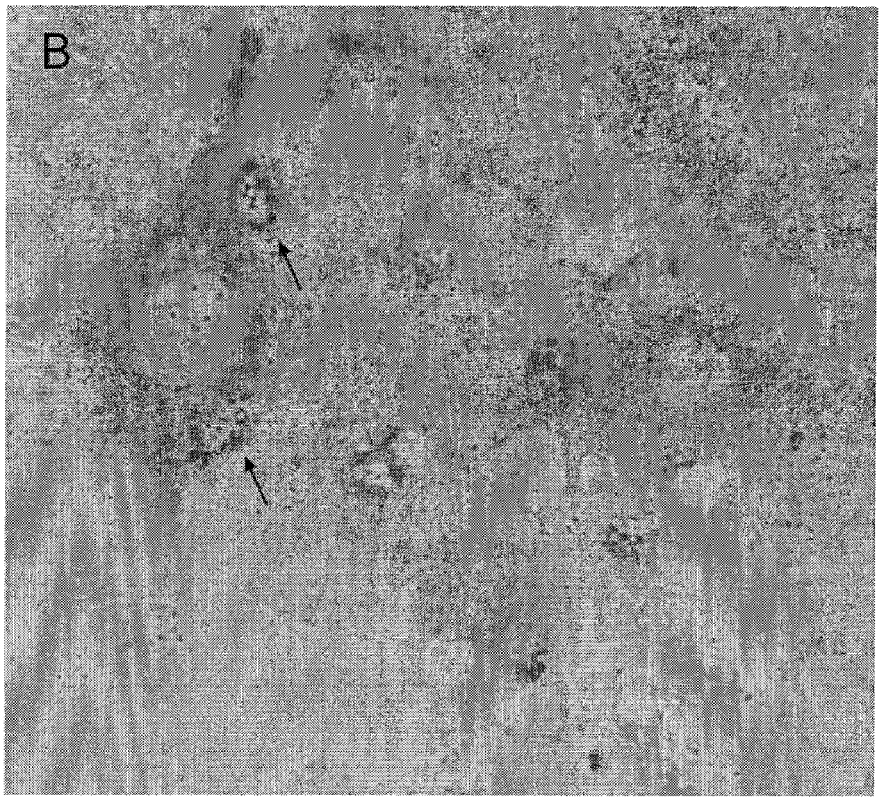

FIG. 5: Microglial reaction in the anterior horn after SNI
A CD11b immunofluorescence for the demonstration of active microglial cells in the ventral horn of the spinal cord after SNI.
B Progranulin mRNA (in situ hybridisation, grey) in activated microglial cells (arrow) next to motor neurons (red, peripherin-immunofluorescence).

Figure 6:
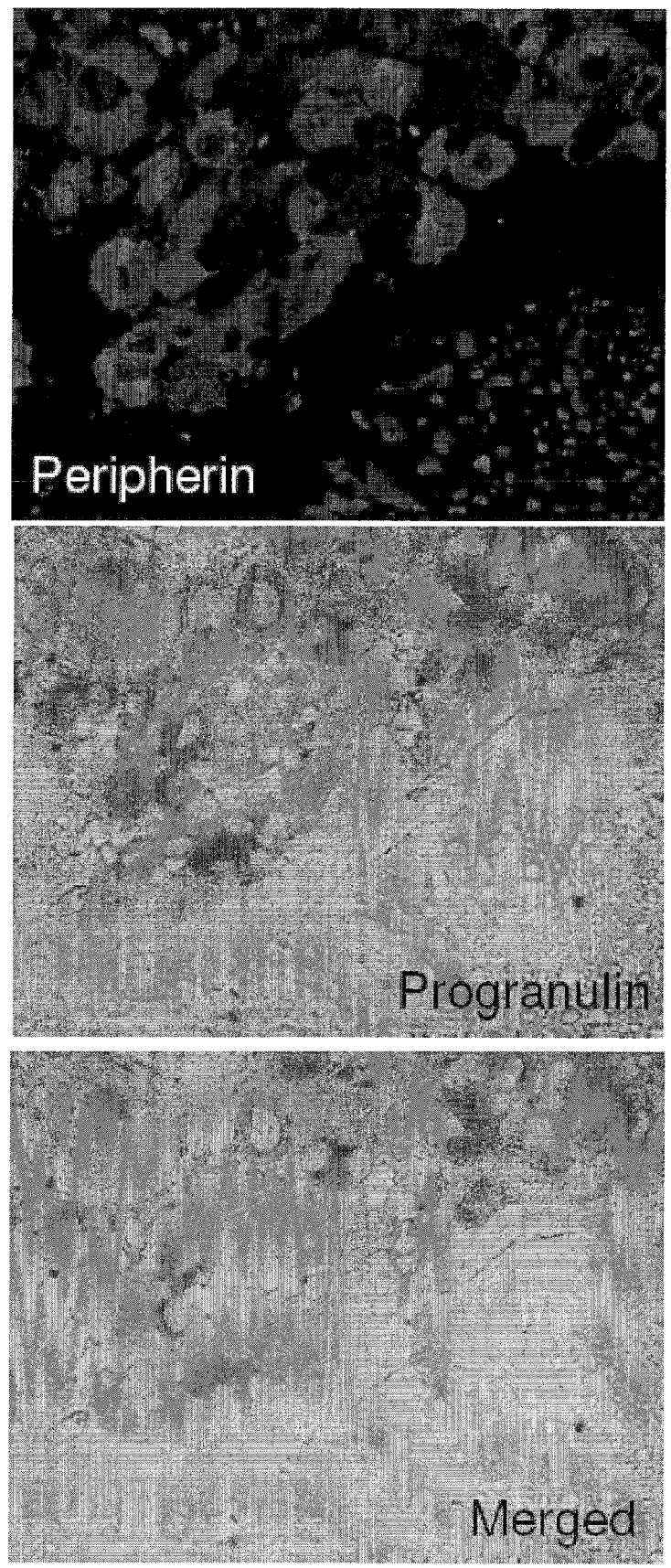

FIG. 6: Neurons of the dorsal ganglia (peripherin IR red) with expression of the progranulin mRNA (in situ hybridisation, grey) after SNI.

Figure 7:
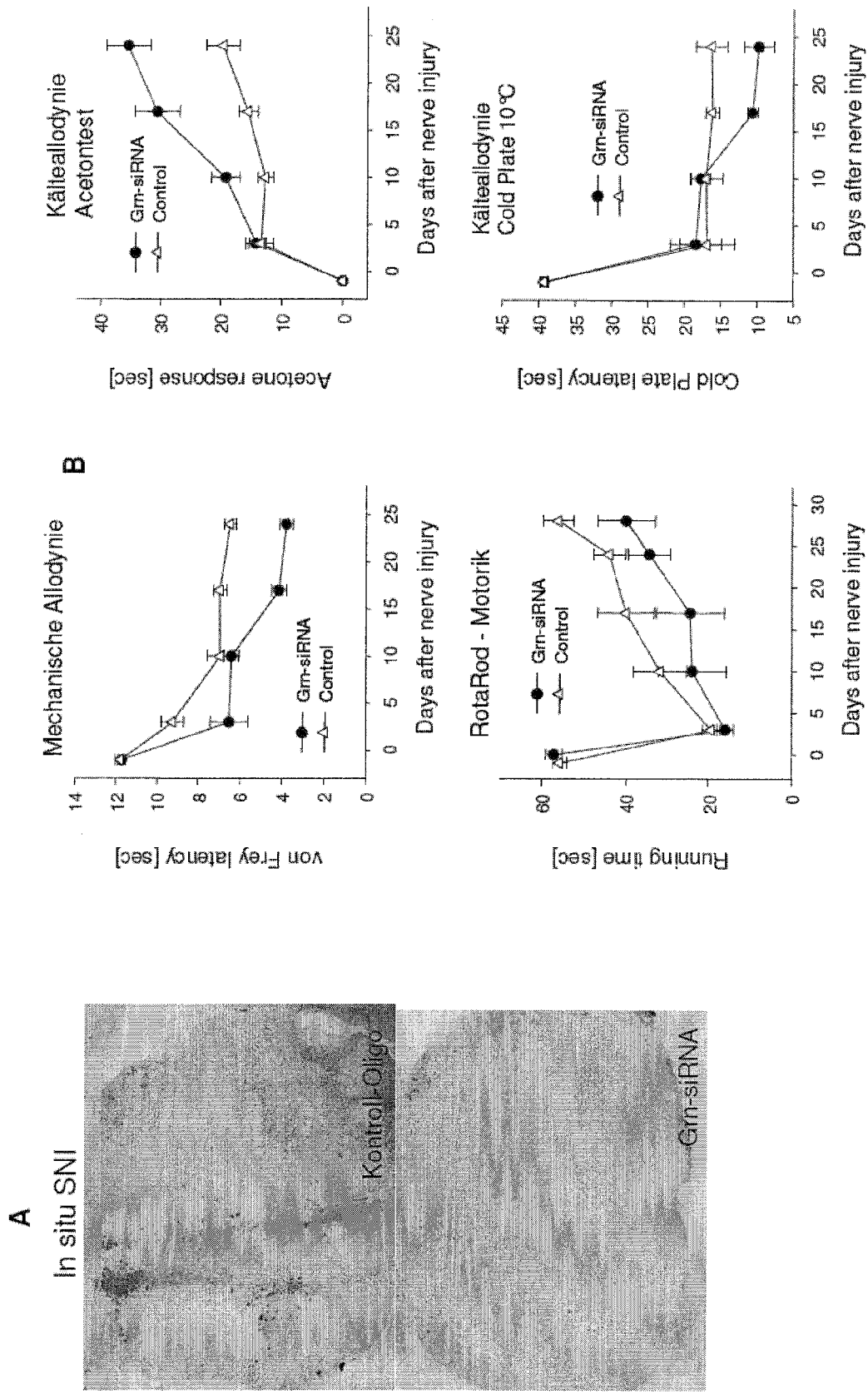

FIG. 7: Progranulin mRNA expression and behaviour of mice upon continuous spinal infusion of progranulin siRNA after SNI.
A Grn mRNA after SNI in the spinal cord upon treatment with Grn siRNA and control-oligonucleotides. The treatment took place using a subcutaneous implanted osmotic Alzet pump via a spinal catheter, ending at the level of L3. Infusion begins immediately after SNI and ends 4 weeks after SNI.
B. Behaviour of the mice (C57Black6) after SNI upon treatment with Grn siRNA or control oligonucleotides in different nociceptive tests and in the rotarod test that measures the motoric performance. Mechanic allodynia was measured by measuring the "withdrawal"-latency with a dynamic von Frey aesthesiometer, the shorter the latency, the stronger the allodynia (top left). Cold-allodynia was recorded in the acetone assay (top right) and with a cold plate at 10° C. (bottom right). In the acetone assay the duration of the reaction (licking, shaking, lifting) of the paw after application of a drop of acetone on the sole of the foot was measured, the longer the reaction, the stronger the allodynia. The reaction latency after exposition against cold is measured with the cold plate, the shorter the stronger the allodynia. It is measured in the rotarod test, how long the mouse runs on a turning cylinder without falling down. Measured is the motoric coordination and exhaustion as well as ability for compensation after neuronal lesion. The behavioural experiments show an increase of the allodynia and impaired motoric recovery upon treatment with Grn siRNA. The treatment of mice by spinal infusion of progranulin siRNA blocks the up-regulation of the progranulin occurring after SNI and leads to an increase of the pain-like behaviour in mice. In addition that recovery of the motoric function in the rotarod test is slightly slower than in control animals that were treated with control-oligonucleotides.

Figure 8:
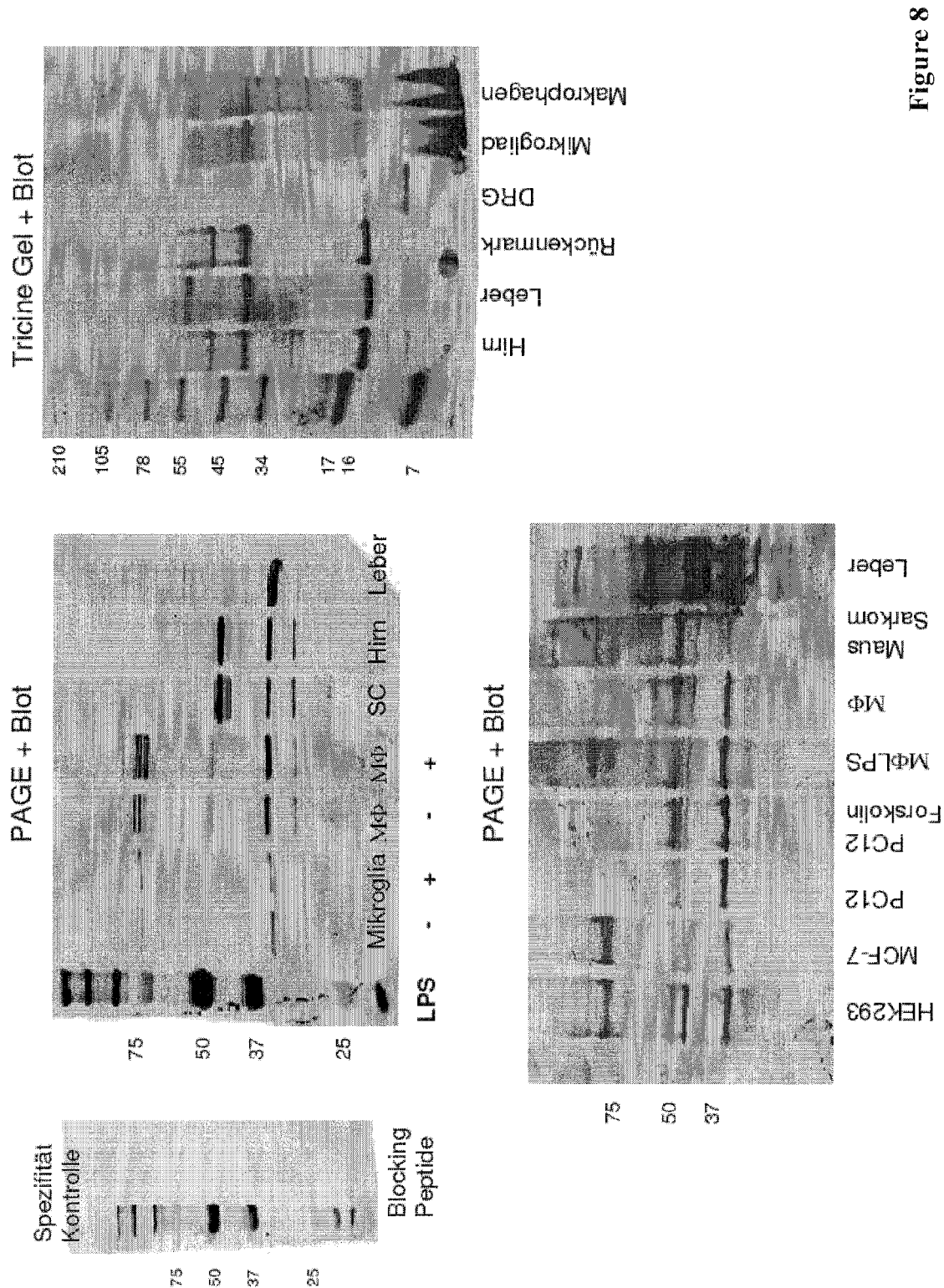

FIG. 8: Progranulin/granulin protein expression in cells and mouse tissues. Western blot with N19-antibody (SantaCruz Biotechnology) directed against progranulin, granulin 1, 2, and 7. Molecular weight of the glycosylated progranulin 88 kDa, the individual granulins 6 kDa. Tricine gels were used for separating the small peptides. Abbreviations: MF macrophages, LPS lipopolysaccharide, SC spinal cord, DRG dorsal ganglia, HEK293 human embryonic kidney cells, MCF-7 breast cancer cells, PC 12 phaeochromocytoma cells (neuron-like), PAGE polyacrylamide-gel-electrophoresis.

EXAMPLES

In the following the invention is explained by means of the experiments as described here with reference to the results as depicted in the Figures.
Methods Progranulin
Models of Neuropathy and RNAi Treatment
Adult C57Bl6 mice were used. In the spared nerve injury (SNI) model two branches of the nervus (N.) *ischiadicus*, namely the *N. peronaeus* and *N. tibialis* were ligated and distally cut through. The *N. suralis* remains intact. Using an osmotic pump (Alzet osmotic pump 2004; 0.25 µl/h) silencer RNA (stealth RNAi, Invitrogen) for acrogranin was intrathecally infunded continuously via a spinal catheter (PTFE sublite wall tubing; OD/ID 0.15 mm/0.05 mm). The tip of the catheter was placed at the level of the lumbal cord, the osmotic pump was fixed in the subcutaneous tissue. The infusion started directly after SNI operation and lasted for 4 weeks. A mixture of three different acrogranin RNAis (1 nmol per each mouse for the duration of 4 weeks) or control RNAis, respectively, was used. In addition, an FITC labelled dummy-RNAi (20 nmol) was infunded for a later immunohistological localisation. The infusion solution consisted of Ringer solution with 1:40 diluted lipofectamin (195 µl Ringer+5 µl lipofecatmin per pump).
Nociceptive Behaviour
The animals were familiarized with the test cages for 3×30 min. The measurement of the behaviour was performed without the knowledge about the treatment. The reaction latency for mechanic stimulation of the hindpaw was measured using a dynamic von Frey device (Dynamic aesthesiometer, UgoBasile, Italien). Using a "cold plate" (4° C.) the pain sensitivity against cold was measured by counting the adverse reactions (licking, jumping, lift leg) over a period of 90 sec. Using a 52° C. "hot plate" the pain sensitivity against heat was determined by measuring the latency until the first reaction. The cut-off latency was 30 sec, in order to avoid issue damages. In the rotarod test the motoric coordination or the motoric recovery after neuronal lesion, respectively, was measured (90 sec cut-off).

Microarrays

The total-RNA was extracted from homogenised spinal cord or DRG tissue by means of Qiagen RNA-extraction kit, and transcribed into DNA. cDNA fragments were amplified by means of PCR and ligated into the pCR4 vector (TA Cloning Kit, Invitrogen). Biotinylated cRNA was produced through in vitro transcription and used for the hybridisation of the Affymetrix RGU34A chips.

Quantitative RT-PCR

The total-RNA was extracted from homogenised spinal cord or DRG tissue by means of Qiagen RNA-extraction kit, and transcribed into DNA. The quantitative real-time rt-PCR was performed using the Sybr-Green detection systems in accordance with the manual of the provider (Applied Biosystems). Primer sets were selected with Primer Express. The amplification of specific PCR-products was verified by agarose gelelectrophoresis.

Western Blot

Spinal cord or DRG tissue was homogenized in Phospho-Safe extraction buffer (Novagen), the homogenate was centrifuged (40.000 g, 20 min) and the proteins in the supernatant were separated by polyacrylamide or tricine gel electrophoresis, respectively. The proteins were transferred onto nitrocellulose-membranes by means of wet-blot, blocked in PBST-5° A) milk (0.05 Tween 20 in 1 mol/l PBS with 5% low-fat milk powder), incubated over night with antibodies against acrogranin (1:1000 in PBST), washed, incubated with secondary antibodies 2 hours (h) at room temperature and evaluated using the Odyssee Western Blot Scanner.

In Situ Hybridisation

Mice were sacrificed through $CO_2$ and exsanguination, L4/5 DRGs and spinal cord were rapidly removed, embedded in OCT, frozen on dry ice, and cut with a cryotome into 14 µm sections. Sections were postfixed in 4% paraformaldehyde, and acetylated. DIG-labelled ribosamples were generated through in vitro transcription of cDNA fragments and incorporation of digoxigenin-labelled dUTP (Dig-labelling kit, Roche). The sections were prehybridized for 2 h at RT in prehybridization solution (5×SSC, 50% formamide, 2×Denhardt's, 500 µg/ml herring sperm DNA, 250 µg/ml yeast tRNA) and subsequently hybridized with 250 ng/ml riboprobe (antisense and sense) in prehybridization solution for 16 h at 72° C. in the oven. The sections were washed in 0.2×SSC at 68° C. for 2 h, incubated with anti-sig-AP antibody (1:1000 in 1% blocking reagent (Roche) in 0.1 mol/l maleic acid buffer) at 4° C. overnight and developed with NBT/BCIP/Levamisol (Boehringer Mannheim). The sections were embedded in glycerol/gelatine or further developed through post in situ immunofluorescence with respective antibodies.

Immunofluorescence

For a fixation the animals were intracardially perfused with 1×PBS and subsequently 4% paraformaldehyde. The tissue was prepared, post-fixed in 4% PFA for 2 h, protected against cryoartifacts over night in 20% sucrose in 1×PBS, embedded in OCT and 12 or 14 µm sections, respectively, were cut with a cryotome. The sections were blocked in 1×PBS with 0.03% Triton X-100 and 1% blocking reagent (Roche) for 2 h at RT, incubated over night with primary antibodies in blocking-solution (see above) at 4° C., washed, then incubated with species-specific Cy3, Alexa-488 or FITC labelled secondary antibodies in blocking-solution for 2 h at RT, washed again, treated with 0.02% Sudan black for a reduction of the autofluorescence, and embedded with Vectashield. The analysis took place at the fluorescence (Nikon) or laser scanning microscope (Zeiss), respectively.

The following primary antibodies were used: Mouse NF200 1:4000 (Sigma), mouse CGRP 1:1000 (Sigma), rabbit ATF-3 1:300 (SantaCruz). FITC-labeled griffonia simplicifolia isolectin B4 (Sigma) 1:500, rabbit GFAP (1:1000, Chemicon), rabbit anti-peripherin (1:1000, Chemicon), rabbit Iba-1 (1:500, DAKO).

After a peripheral neuronal damage a microglial activation occurs in the ipsilateral spinal cord, which is important for the generation of neuropathic pain. These activated microglial cells exhibit a strong expression of progranulin, as shown by microarray (FIG. 2), QRT-PCR (FIG. 2), Western Blot (FIG. 2), and in situ hybridization (FIG. 3). DRG- and motor neurons that are directly damaged by the neuronal lesions exhibit a weaker expression (FIG. 3-4).

The invention claimed is:

1. A method for treating neuropathic pain, wherein said method comprises administering, to a subject in need of such treatment, a therapeutically-effective amount of a neuroprotective granulin-like compound comprising amino acid sequence having at least 90% sequence identity to SEQ ID NO:11, or a fragment of the granulin-like compound, wherein the granulin-like compound and the functional fragment thereof have neuroprotective activity, and wherein neuropathic pain is treated.

2. The method according to claim 1, wherein the neuroprotective granulin-like compound comprises an amino acid sequence having at least 95% sequence identity to SEQ ID NO:11.

3. The method according to claim 1, wherein the neuroprotective granulin-like compound comprises the amino acid sequence of SEQ ID NO:11.

4. The method according to claim 1, wherein the functional fragment of the granulin-like compound comprises at least 30 amino acids.

5. The method according to claim 1, wherein the functional fragment of the granulin-like compound comprises at least 50 amino acids.

6. The method according to claim 1, wherein the method comprises administering a therapeutically effective amount of a neuroprotective granulin-like compound comprising the amino acid sequence of SEQ ID NO:11.

* * * * *

UNITED STATES PATENT AND TRADEMARK OFFICE
CERTIFICATE OF CORRECTION

PATENT NO. : 8,367,616 B2  
APPLICATION NO. : 12/668147  
DATED : February 5, 2013  
INVENTOR(S) : Irmgard Tegeder et al.

Page 1 of 1

It is certified that error appears in the above-identified patent and that said Letters Patent is hereby corrected as shown below:

In the Specifications

Column 7,

Lines 31-32, "PBST-5 ° A) milk" should read --PBST-5 % milk--

Column 7,

Line 32, "0.05 Tween" should read --0.05 % Tween--

Column 20,
Line 64, "or a fragment of the granulin-like" should read
--or a functional fragment of the granulin-like--

Signed and Sealed this
Seventh Day of May, 2013

Teresa Stanek Rea
*Acting Director of the United States Patent and Trademark Office*